(12) United States Patent
Nie et al.

(10) Patent No.: US 11,751,785 B2
(45) Date of Patent: Sep. 12, 2023

(54) TESTING METHOD AND TESTING SYSTEM FOR HUMAN STRESS REACTION, AND COMPUTER-READABLE STORAGE MEDIUM

(71) Applicant: Tsinghua University, Beijing (CN)

(72) Inventors: Bingbing Nie, Beijing (CN); Quan Li, Beijing (CN); Qing Zhou, Beijing (CN)

(73) Assignee: TSINGHUA UNIVERSITY, Beijing (CN)

(*) Notice: Subject to any disclaimer, the term of this patent is extended or adjusted under 35 U.S.C. 154(b) by 547 days.

(21) Appl. No.: 17/006,419

(22) Filed: Aug. 28, 2020

(65) Prior Publication Data

US 2020/0390380 A1    Dec. 17, 2020

Related U.S. Application Data

(63) Continuation of application No. PCT/CN2019/101880, filed on Aug. 22, 2019.

(30) Foreign Application Priority Data

Jun. 5, 2019 (CN) .......................... 201910486529.1

(51) Int. Cl.
*G08B 23/00* (2006.01)
*A61B 5/18* (2006.01)
(Continued)

(52) U.S. Cl.
CPC .............. *A61B 5/18* (2013.01); *A61B 5/1038* (2013.01); *A61B 5/165* (2013.01);
(Continued)

(58) Field of Classification Search
CPC ......... A61B 5/18; A61B 5/1038; A61B 5/165; A61B 2503/22; G02B 27/0172;
(Continued)

(56) References Cited

U.S. PATENT DOCUMENTS

2015/0328458 A1    11/2015   Rodriguez et al.
2018/0024019 A1*    1/2018   Schagerl .................. G01L 5/28
                                                    434/69

(Continued)

FOREIGN PATENT DOCUMENTS

CN    205983964    2/2017
CN    107928685    4/2018
(Continued)

OTHER PUBLICATIONS

International Search Report of PCT/US2018/012421.

*Primary Examiner* — Naomi J Small

(57) ABSTRACT

The present disclosure relates to a testing method and a testing system for a human stress reaction, and a computer-readable storage medium. The testing method for the human stress reaction includes acquiring position information and visual field information of a testee in a virtual road traffic scene after the virtual road traffic scene is established; guiding the testee into a test zone when the testee is within a test-waiting zone and when a visual field direction of the testee faces the test zone, and simultaneously, starting acquiring stress reaction data of the testee; controlling a virtual reality environment module to create a virtual stress event in the test zone after it is determined that the testee is within the test zone, and applying a stimulation to the testee, such that the testee make a stress reaction.

16 Claims, 5 Drawing Sheets

(51) Int. Cl.
- *A61B 5/103* (2006.01)
- *A61B 5/16* (2006.01)
- *G02B 27/01* (2006.01)
- *G06F 3/01* (2006.01)
- *G06F 3/16* (2006.01)
- *G09B 9/05* (2006.01)
- *G09B 9/052* (2006.01)

(52) U.S. Cl.
CPC ......... *G02B 27/0172* (2013.01); *G06F 3/015* (2013.01); *G06F 3/167* (2013.01); *G09B 9/05* (2013.01); *G09B 9/052* (2013.01); *A61B 2503/22* (2013.01)

(58) Field of Classification Search
CPC .......... G06F 3/015; G06F 3/167; G09F 3/167; G09B 9/05; G09B 9/052
USPC ......................................................... 340/576
See application file for complete search history.

(56) References Cited

U.S. PATENT DOCUMENTS

| | | | |
|---|---|---|---|
| 2018/0190376 A1 | 7/2018 | Hill et al. | |
| 2018/0197344 A1* | 7/2018 | Takano | G06T 5/001 |
| 2020/0294311 A1* | 9/2020 | Holz | H04N 13/271 |

FOREIGN PATENT DOCUMENTS

| | | |
|---|---|---|
| CN | 107957772 | 4/2018 |
| CN | 108091203 | 5/2018 |
| CN | 108109673 | 6/2018 |
| CN | 108113686 | 6/2018 |
| CN | 108542404 | 9/2018 |
| CN | 108968989 | 12/2018 |
| CN | 109044374 | 12/2018 |
| CN | 109414164 | 3/2019 |
| WO | WO2018129211 | 7/2018 |

* cited by examiner

TESTING METHOD AND TESTING SYSTEM FOR HUMAN STRESS REACTION, AND COMPUTER-READABLE STORAGE MEDIUM

CROSS-REFERENCE TO RELATED APPLICATIONS

The present application is a continuation application of the PCT application No. PCT/CN2019/101880, filed on Aug. 22, 2019 and titled "Testing Method and Testing System for Human Stress Reaction, and Computer-Readable Storage Medium", which claims the priority of the Chinese patent application No. 201910486529.1, filed on Jun. 5, 2019 and titled "Testing Method and Testing System for Human Stress Reaction", and the contents of both applications are incorporated by reference herein in their entirety.

TECHNICAL FIELD

The present application relates to the technical field of road traffic safety and development of automobile safety, and in particular, to a testing method and a testing system for human stress reaction, and a computer-readable storage medium.

BACKGROUND

Road traffic safety is a major public health problem worldwide. Pedestrians belong to a vulnerable group in the road traffic environment and account for a high proportion of total deaths in traffic accidents. The stress reactions of the pedestrians in traffic accidents directly affect their risk of injury. The human stress reaction refers to a kind of non-specific reaction caused by various stressful stimuli (stressors), and will cause changes in human physiology, psychology, and behaviors. A benignant human stress reaction is beneficial for the body of human to fight against or escape from an emergency. A pernicious human stress reaction may cause pathological changes in the body and even death. The study of a neurophysiological reaction and a biomechanical behavior pattern, which are related to the human stress reaction, is of great significance to the survival and evolution of organisms. The study of the human stress reaction is of great practical significance in the field of road traffic safety.

However, current testing methods for the human stress reactions are too limited to be performed for practical stimuli in dangerous situations. Traditional tests for the human stress reactions are generally performed by stimuli research methods in the fields of neuroscience and psychology through simple visual or contact stimulus.

However, the traditional testing method for the human stress reaction has a severe problem that the real stress reaction of the testee cannot be obtained the moment a road traffic accident occurs. As for the experimental study of the human stress reaction in the field of neuroscience and psychology, the stimulus signal is single, and a three-dimensional scene close to the real world cannot be established to act as a stimulus signal to stimulate the testee; it is difficult to design complex conditions in which the stimulus occurs, so it is impossible to study the human stress reaction mechanism under multiple conditions and multiple scenes. In studying road traffic safety and developing products for road traffic safety, it is necessary to investigate road traffic accidents. The safety is difficult to guarantee, therefore it is difficult to carry out a test for the living pedestrian testee, and it is impossible to obtain the pedestrian stress reaction information immediately before the pedestrian accident takes place through the road traffic accident investigation.

SUMMARY

Based on this, according to various embodiments of the present application, a testing method and a testing system for human stress reaction, and a computer-readable storage medium are provided.

The testing method for the human stress reaction provided by the present application includes:

sending a request for establishing a virtual road traffic scene to a virtual reality environment module;

acquiring position information and visual field information of a testee in the virtual road traffic scene after the virtual reality environment module establishes the virtual road traffic scene;

guiding the testee into a test zone, if the testee is within a test-waiting zone in the virtual road traffic scene, and if a visual field direction of the testee faces the test zone in the virtual road traffic scene, and starting acquiring stress reaction data of the testee simultaneously; and controlling the virtual reality environment module to create a virtual stress event in the test zone after it is determined that the testee is within the test zone, and applying a stimulation to the testee, such that the testee make a stress reaction.

The present application further provides a testing system for a human stress reaction, including:

a virtual reality environment module configured to establish a virtual road traffic scene;

a virtual scene display device worn on a head of the testee and configured to present the virtual road traffic scene in brains of the testee; and a virtual scene control module, connected to the virtual reality environment module and the virtual scene display device respectively, and comprising a storage and one or more processors, wherein computer-readable instructions are stored in the storage, and when the computer-readable instructions are executed by the one or more processors, the one or more processors perform steps of:

sending a request for establishing a virtual road traffic scene to a virtual reality environment module;

acquiring position information and visual field information of a testee in the virtual road traffic scene after the virtual reality environment module establishes the virtual road traffic scene;

guiding the testee into a test zone, if the testee is within a test-waiting zone in the virtual road traffic scene, and if a visual field direction of the testee faces the test zone in the virtual road traffic scene, and simultaneously, starting acquiring stress reaction data of the testee;

controlling the virtual reality environment module to create a virtual stress event in the test zone after it is determined that the testee is within the test zone, and applying a stimulation to the testee, to get the testee make a stress reaction.

The present application further provides a computer readable storage medium, having computer-readable instructions stored thereon. The computer-readable instructions, when executed by one or more processors, cause the one or more processor to perform steps of:

sending a request for establishing a virtual road traffic scene to a virtual reality environment module;

acquiring position information and visual field information of a testee in the virtual road traffic scene after the virtual reality environment module establishes the virtual road traffic scene;

guiding the testee into the test zone, if the testee is within a test-waiting zone in the virtual road traffic scene, and if a visual field direction of the testee faces a test zone in the virtual road traffic scene, and simultaneously, starting acquiring stress reaction data of the testee;

controlling the virtual reality environment module to create a virtual stress event in the test zone after it is determined that the testee is within the test zone, and applying a stimulation to the testee, to get the testee make a stress reaction.

Details of one or more embodiments of the present application are illustrated in the accompanying drawings and description below. Other features, objectives, and advantages of the present application are apparent in the description, in the drawings, and in the claims.

BRIEF DESCRIPTION OF THE DRAWINGS

In order to describe the embodiments of the present application or the technical schemes of the prior art more clearly, the present application will be described briefly with reference to the drawings used in describing the embodiments or the prior art. It is obvious that the drawings described hereafter are merely some embodiments of the present invention. For those skilled in the art, other figures can be obtained according to the figures provided hereafter without any creative work.

DETAILED DESCRIPTION OF THE EMBODIMENTS

In order to make the objectives, technical solutions and advantages of the present application clearer and better understood, the present application will be further described in detail below with reference to the accompanying drawings and embodiments. It should be understood that the specific embodiments described herein are merely illustration of the present application, but not intended to limit the present application.

The present application provides a testing method and a testing system for a human stress reaction, and a computer-readable storage medium.

It should be noted that the testing method and the testing system for the human stress reaction, and the computer-readable storage medium provided by the present application do not limit their application fields and application scenes. Optionally, the testing method and the testing system for the human stress reaction, and the computer-readable storage medium provided by the present application are applied to a field of road traffic safety.

The present application provides a testing method for a human stress reaction. The testing method for the human stress reaction provided by the present application does not limit its execution subject. Optionally, the testing method for the human stress reaction is carried out through virtual reality technology. Optionally, the execution subject of the testing method for the human stress reaction can be a virtual scene control module 30 in the testing system for the human stress reaction. Specifically, the execution subject can be one or more processors in the virtual scene control module 30.

Figure 1:
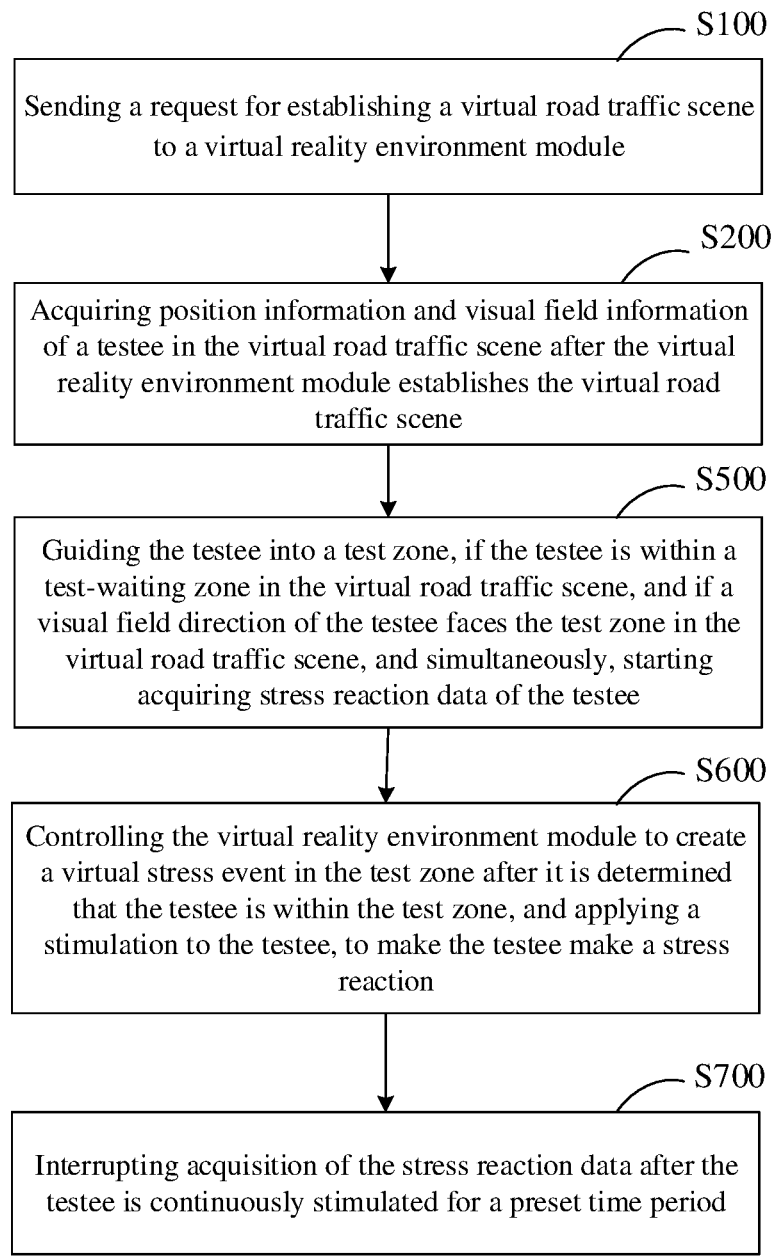
FIG. 1 is a schematic flowchart of a testing method for a human stress reaction according to an embodiment of the present application.
Figure 2:
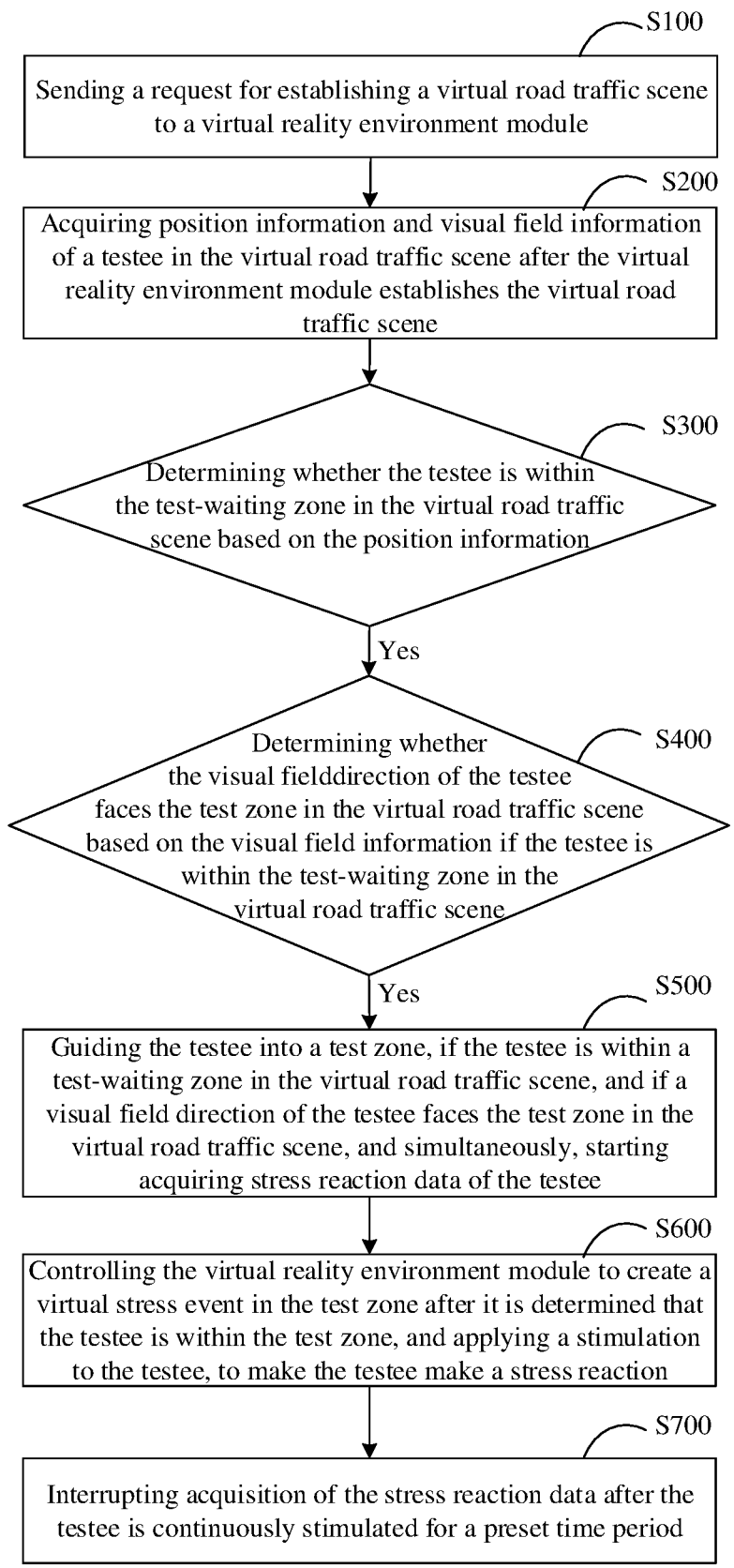
FIG. 2 is a schematic flowchart of a testing method for a human stress reaction according to another embodiment of the present application.

As shown in FIGS. 1 and 2, in an embodiment of the present application, the testing method for the human stress reaction includes following steps S100 to S700.

At step S100, send a request for establishing a virtual road traffic scene 100 to a virtual reality environment module 10.

Specifically, the virtual scene control module 30 sends the request for establishing the virtual road traffic scene 100 to the virtual reality environment module 10. The virtual reality environment module 10 establishes the virtual road traffic scene 100 based on the request for establishing the virtual road traffic scene 100. The virtual road traffic scene 100 can include one or more of virtual buildings, virtual moving vehicles, virtual pedestrians, and traffic lanes. The virtual road traffic scene 100 is presented on a virtual scene display device 20 worn by a testee. The virtual scene display device 20 can be a headset virtual reality display device (headset VR display device). When the testee wears the virtual scene display device 20, the testee can be in the virtual road traffic scene 100 and has a feeling of being in a real road traffic environment.

At step S200, acquire position information and visual field information of the testee in the virtual road traffic scene 100 after the virtual reality environment module 10 establishes the virtual road traffic scene 100.

Figure 3:
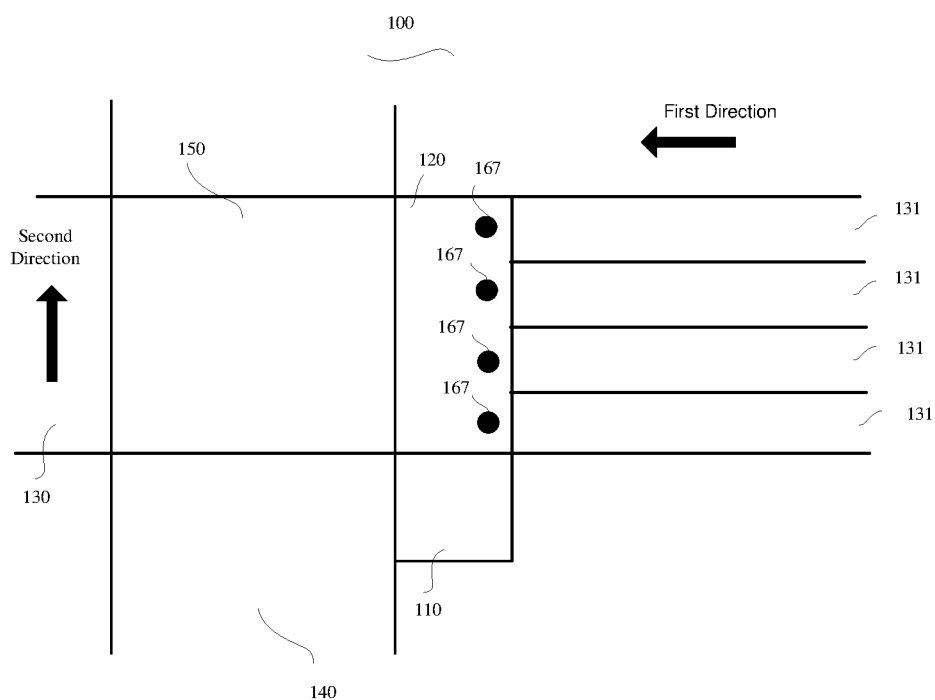
FIG. 3 is a schematic structural diagram illustrating a virtual road traffic scene in the testing method for the human stress reaction according to an embodiment of the present application.

Specifically, the virtual road traffic scene 100 corresponds to an actual activity area where the testee is located. As shown in FIG. 3, the virtual road traffic scene 100 includes a test-waiting zone 110 and a test zone 120. The actual activity area includes a test-waiting activity area and a test activity area. The test-waiting zone 110 corresponds to the test-waiting activity area. The test zone 120 corresponds to the test activity area. For example, when the testee is standing in the test-waiting activity area, the testee is in the test-waiting zone 110 in the virtual road traffic scene 100 perceived by the testee. When the testee moves from the test-waiting activity area to the test activity area, the testee moves from the test-waiting zone 110 to the test zone 120 in the virtual road traffic scene 100 perceived by the testee.

Optionally, the body of the testee is provided with a position feature acquisition module 70 which is configured to acquire the position information and the visual field information of the testee in the virtual road traffic scene 100. Specifically, the position feature acquisition module 70 can include a locator. The locator is connected to the virtual scene control module 30. The locator can acquire, in real time, the position information of the testee in the virtual road traffic scene 100, and send the position information to the virtual scene control module 30.

The position feature acquisition module 70 can include a visual field detection device. The visual field detection device can be installed on the testee's head, and is configured to acquire, in real time, the visual field information of the testee in the virtual road traffic scene 100. The visual field information can include a visual field direction and/or a visual field range of the testee. The visual field detection device can acquire the visual field information in multiple ways. Optionally, the visual field detection device can acquire a motion track of the testee's pupils, to determine the visual field information.

At step S300, determine whether the testee is within the test-waiting zone 110 in the virtual road traffic scene 100 based on the position information.

Figure 4:
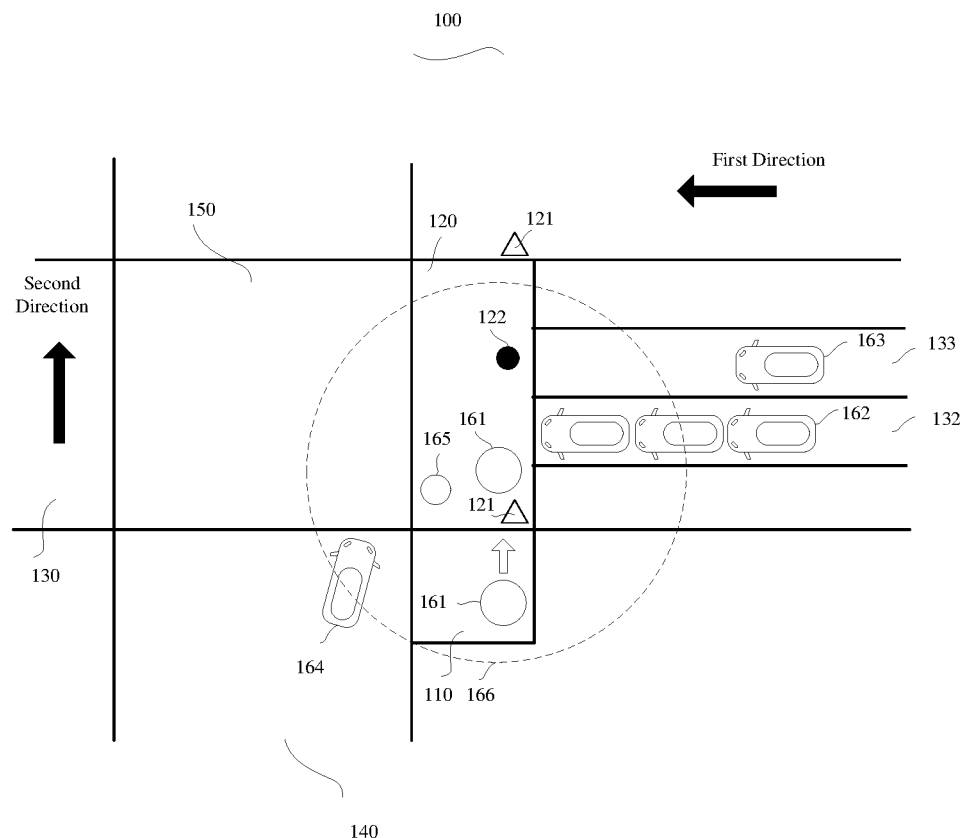
FIG. 4 is a schematic structural diagram illustrating a virtual road traffic scene in the testing method for the human stress reaction according to another embodiment of the present application.

Specifically, the test-waiting zone 110 is configured to make preparations for a human stress reaction test. Specifically, as shown in FIGS. 3 and 4, the virtual scene control module 30 determines whether a position 161 of the testee is within the test-waiting zone 110. If the testee is within the test-waiting zone 110 in the virtual road traffic scene 100, the virtual scene control module 30 determines that the testee is ready for subsequent test steps. If the testee is not within the test-waiting zone 110 in the virtual road traffic scene 100, the virtual scene control module 30 determines that the testee deviates from the actual activity area. It can be understood that the testee may deviate from the scope of the virtual road traffic scene 100 in subsequent test processes.

At step S400, determine whether the visual field direction of the testee faces the test zone 120 in the virtual road traffic scene 100 based on the visual field information if the testee is within the test-waiting zone 110 in the virtual road traffic scene 100.

Specifically, it has been mentioned above that, if the testee is within the test-waiting zone 110, the virtual scene control module 30 determines that the testee is within the test-waiting zone 110. However, a virtual stress event in the virtual road traffic scene 100, which actually causes the testee to make a stress reaction, is established in the test zone 120, but not in the test-waiting zone 110. Therefore, only if it is confirmed that the visual field direction of the testee is facing the test zone 120, can the testee be guided into the test zone 120, to trigger the virtual stress event. It can be understood that, further, the virtual scene control module 30 determines whether the visual field direction of the testee faces the test zone 120 based on the visual field information.

In addition, if the testee is not within the test-waiting zone 110, the virtual scene control module 30 can control a voice instructing module 80 to send out a voice instruction to guide the testee into the test-waiting zone 110. Of course, the testee can also be manually pulled into the test-waiting zone 110 via a tester's physical contact with the testee.

At step S500, guide the testee into the test zone 120 if the visual field direction of the testee faces the test zone 120 in the virtual road traffic scene 100, and start acquiring stress reaction data of the testee simultaneously.

Specifically, if the visual field direction of the testee faces the test zone 120, the virtual scene control module 30 determines that the testee is fully prepared for testing, and guides the testee into the test zone 120. A data acquisition device is provided on the testee. The virtual scene control module 30 sends an instruction of starting acquiring the stress reaction data to the data acquisition device. The data acquisition device turns on the data acquisition interface according to the above instructions, and starts acquiring various stress reaction data of the testee.

At step S600, control the virtual reality environment module 10 to create a virtual stress event in the test zone 120 after it is determined that the testee is within the test zone 120, and apply a stimulation to the testee, such that the testee makes a stress reaction.

Specifically, between the step S500 and the step S600, a step of determining whether the testee is within the test zone 120 can be further included, and the step includes:

determining whether the testee is within the test zone 120, and if the testee is within the test zone 120, performing the step S600. The virtual stress event is an event the testee cannot expect. The virtual stress event can be various.

At step S700, interrupt acquisition of the stress reaction data after the testee is continuously stimulated for a preset time period.

Specifically, the preset time period is set by the tester.

In this embodiment, in the testing method for the human stress reaction, the request for establishing the virtual road traffic scene 100 is sent to the virtual reality environment module 10, to establish the virtual road traffic scene 100, such that the testee is in an immersive reality. Determine whether the testee is in the virtual road traffic scene 100 based on the position information and the visual field information of the testee in the virtual road traffic scene 100. Under the condition that the safety of the testee is ensured, the testee is stimulated to make a stress reaction. By acquiring, in real time, the stress reaction data of the testee in dangerous situations, the real stress reaction data of a human during the occurrence of a traffic accident can be monitored and recorded. The testing method for the human stress reaction provided by the present application, under the condition that the safety of the testee is ensured, realizes the test for the real stress reaction of the testee the moment the road traffic accident occurs, and the obtained stress reaction data are reliable and effective.

As shown in FIG. 3 and FIG. 4, in an embodiment of the present application, the virtual road traffic scene 100 includes a first lane 130, a second lane 140, a test zone 120, and traffic lights 121. The first lane 130 extends in a first direction. The second lane 140 extends in a second direction. The first direction is perpendicular to the second direction. The first lane 130 and the second lane 140 intersect to form an intersection 150. The test zone 120 is disposed on the first lane 130. The test zone 120 extends in the second direction. The test zone 120 runs across the first lane 130. The traffic lights 121 are disposed at the test zone 120.

The first lane 130 can include a plurality of sub-lanes 131 arranged in parallel with each other. Each of the sub-lanes 131 extends in the first direction. The test zone 120 can be arranged to be adjacent to the intersection 150. The traffic lights 121 are provided to show the testee a traffic situation of the test zone 120.

Specifically, as shown in FIG. 3 and FIG. 4, the first lane 130 and the second lane 140 constitute a common intersection-type lane environment. The test zone 120 is disposed on the first lane 130 and runs across the first lane 130. The test zone 120 is similar to a crosswalk with a zebra crossing. The traffic lights 121 are disposed at the test zone 120. One or more traffic lights 121 are provided. Optionally, the traffic lights 121 can be red and green lights. In this embodiment, the test-waiting zone 110 can be arranged adjacent to the test zone 120. The visual field direction of the testee is the second direction and faces the test zone 120. The testee goes from the test-waiting zone 110 and slowly moves to the test zone 120 in the second direction. In the process, the position 161 of the testee is constantly changing. The tester can send out a target instruction, for example, "please cross the road", to the testee through the voice instructing module 80, so as to guide the testee across the test-waiting zone 110.

In this embodiment, by arranging the first lane 130, the second lane 140, the test zone 120, and the traffic lights 121, the virtual road traffic scene 100 close to reality is established, such that the testee's sense of reality is greatly enhanced, thereby effectively simulating the real road traffic environment. The virtual road traffic scene 100 in this embodiment provides an environmental base for subsequent testing steps for the human stress reaction.

In an embodiment of the present application, the step S500 includes the following steps S510 to S590:

At step S510, if the visual field direction of the testee faces the test zone 120 in the virtual road traffic scene 100, send an instruction to the virtual reality environment module 10. The instruction is configured to control the traffic lights 121 to show an impassable state. An auxiliary vehicle 162 is controlled to appear and travel on a first sub-lane 132 of the first lane 130 at a first preset travelling speed.

Specifically, the traffic lights 121 can be red and green traffic lights. The controlling the traffic lights 121 to show the impassable state can specifically include controlling the traffic lights 121 to display a red light, to warn the testee that the test zone 120 is in an impassable state. At this time, the testee stands still at an edge of the test zone 120. The first preset travelling speed is preset by the tester.

At step S530, acquire a position of the auxiliary vehicle 162. Calculate a straight-line distance from the position of the auxiliary vehicle 162 to the test zone 120 in the first direction based on the position of the auxiliary vehicle 162.

Specifically, the auxiliary vehicle 162 is set to stop when it travels to the edge of the test zone 120, so as to make the virtual road traffic scene 100 simulate a real driving environment. It can be understood that the straight-line distance from the position of the auxiliary vehicle 162 to the test zone 120 is the distance traveled by the auxiliary vehicle 162 from its current position to the edge of the test zone 120. In this embodiment, the position of the auxiliary vehicle 162 changes in real time, and the position of the test zone 120 is fixed. Therefore, the straight-line distance from the position of the auxiliary vehicle 162 to the test zone 120 can be calculated in real time.

At step S550, determine whether the straight-line distance from the position of the auxiliary vehicle 162 to the test zone 120 is greater than a preset distance.

Specifically, the preset distance is a safe braking distance of the auxiliary vehicle 162. The safe braking distance of the auxiliary vehicle 162 is preset by the tester. The preset distance is a distance traveled by the auxiliary vehicle 162 which decelerates to the speed of 0 at a preset braking deceleration. It can be understood that, if the straight-line distance from the position of the auxiliary vehicle 162 to the test zone 120 is greater than the preset distance, then the auxiliary vehicle 162 is in a safe state, and the auxiliary vehicle 162 continues to travel normally; conversely, if the straight-line distance from the position of the auxiliary vehicle 162 to the test zone 120 is equal to the preset distance, then the auxiliary vehicle 162 is necessarily controlled to stop travelling, that is, the auxiliary vehicle 162 is controlled to "brake"; and if the straight-line distance from the position of the auxiliary vehicle 162 to the test zone 120 is less than the preset distance, then the auxiliary vehicle 162 is necessarily controlled to stop travelling, that is, the auxiliary vehicle 162 is controlled to "brake in advance".

At step S570, if the straight-line distance from the position of the auxiliary vehicle 162 to the test zone 120 is not greater than the preset distance, then the auxiliary vehicle 162 is controlled to stop travelling, and the traffic lights 121 are controlled to show a passable state.

Specifically, the traffic lights 121 can be red and green lights. At this time, the virtual scene control module 30 controls the traffic lights to display green light. At the steps S510 to S570, a scene event that the auxiliary vehicle 162 changes from a travelling state to a stopping state is created, thereby enhancing the real effects of the virtual road traffic scene 100.

At step S590, send an instruction to the voice instructing module 80, to control the voice instructing module 80 to send out a voice instruction. The voice instruction is configured to guide the testee across the test zone 120 at a constant speed.

Specifically, through the voice instructing module 80, the tester can send out the voice instruction, for example, "please cross the road", so as to guide the testee across the test zone 120.

In this embodiment, the scene event, which the auxiliary vehicle 162 changes from a travelling state to a stop, is created, thereby strengthening the real effects of the virtual road traffic scene 100.

In an embodiment of the present application, the step S600 includes the following steps S610 to S630:

At step S610, a target location point 122 is set in the test zone 120. The target location point 122 is one of a plurality of intersection points 167. The intersections 167 are formed by the sub-lanes 131 intersecting with the test zone 120.

Specifically, each of the sub-lanes 131 intersects with the test zone 120, to form an intersection 167. The number of the intersections 167 is equal to the number of the sub-lanes 131. In this embodiment, the virtual stress event is that a testing vehicle 163 appears on any one of the sub-lanes 131, travels in the first direction, and touches the testee. The target location point 122 is a location where the testing vehicle 163 touches the testee. The target location point 122 is set to be one of the plurality of intersections 167, to ensure that the intersection of the traveling track of the testing vehicle 163 and the travelling track of the testee is the target location point 122.

At step S620, acquire position information of the testee and a walking speed of the testee, and calculate a time taken for the testee to reach the target location point 122.

Specifically, in this embodiment, the walking speed of the testee is constant by default. The position information of the testee is a current position of the testee. A straight-line distance from the testee to the target location point 122 can be calculated based on the current position of the testee. The time taken for the testee to reach the target location point 122 can be obtained by the quotient of dividing the straight-line distance from the testee to the target location point 122 by the walking speed of the testee.

Currently, walking experiments can be performed on the testee before the testing, and multiple walking samples are extracted, to establish a walking speed estimation model and estimate the walking speed of the testee. In this way, the walking speed of the testee is known. The time taken for the testee to reach the target location point 122 can be calculated only if the position information of the testee is obtained in the process of testing.

At step S630, control the testing vehicle 163 to appear at an initial position of the testing vehicle and travel on a second sub-lane 133 at a uniform speed of a second preset speed based on the time taken the testee to reach the target location point 122. The initial position of the testing vehicle is disposed on the second sub-lane 133. The second sub-lane 133 intersects with the test zone 120 to form the target location point 122.

The straight-line distance from the initial position of the testing vehicle to the target location point 122 satisfies the following equations, such that the testing vehicle 163 touches the testee at the target location point 122.

$$\begin{cases} X = X_1 + X_2 = V_0 t_1 + \dfrac{V_0^2 - V_1^2}{2a} & \text{Equation 1} \\ t = t_1 + t_2 = t_1 + \dfrac{V_0 - V_1}{a} & \text{Equation 2} \end{cases}$$

wherein, X is a straight-line distance from the initial position of the testing vehicle to the target location point 122. $X_1$ is a first travelling distance of the testing vehicle 163 before it brakes. $X_2$ is a second travelling distance of the testing vehicle 163 after it brakes. $V_0$ is a second preset speed. $V_1$ is a speed of the testing vehicle 163 when it reaches the target location point 122. $t_1$ is a travelling time of the testing vehicle 163 before it brakes. $t_2$ is a braking time of the testing vehicle 163. a is a braking deceleration of the testing vehicle 163. t is the time taken for the testee to reach the target location point 122.

Specifically, in the equation 1 and the equation 2, the straight-line distance X from the initial position of the testing vehicle to the target location point 122 is an unknown to be determined. The braking deceleration a of the testing vehicle 163 is known. The second preset speed $V_0$ is known. The speed $V_1$ of the testing vehicle 163 when it reaches the target location point 122 is known. The time t taken for the testee to reach the target location point 122 is known. The travelling time $t_1$ of the testing vehicle 163 before it brakes is unknown. Therefore, the straight-line distance X from the initial position of the testing vehicle to the target location point 122 can be obtained according to the equation 1 and the equation 2.

In this embodiment, through the above steps S610 to S630, the virtual stress event, in which the testing vehicle 163 touches the testee, is created in the test zone 120 to apply a stimulation to the testee. In this way, not only the testee's safety is guaranteed, but also the stress reaction data of the testee in dangerous situations can be obtained.

In an embodiment of the present application, the first sub-lane 132 is adjacent to the testee. The second sub-lane 133 is far away from the testee, such that the auxiliary vehicle 162 can hide the testing vehicle 163 when the testing vehicle 163 is traveling.

Specifically, the auxiliary vehicle 162 is provided to block the testee's view. The auxiliary vehicle 162 travels on the first sub-lane 132. The testing vehicle 163 travels on the second sub-lane 133. As known from the above description, the first sub-lane 132 and the second sub-lane 133 are parallel to each other. The first sub-lane 132 is adjacent to the testee, and the second sub-lane 133 is far away from the testee, such that the auxiliary vehicle 162 can hide the testing vehicle 163 and stop the testee from seeing the testing vehicle 163 when the testing vehicle 163 is travelling. Further, the unexpectedness of the virtual stress event in which the testing vehicle 163 touches the testee is enhanced, thereby making the acquired stress reaction data more realistic.

One or more auxiliary vehicles 162 can be provided. When only one auxiliary vehicle 162 is provided, the vehicle body length of the auxiliary vehicle 162 is not less than the travelling length of the testing vehicle 163. When multiple auxiliary vehicles 162 are provided, the multiple auxiliary vehicles 162 are connected end to end, and are disposed on the first sub-lane 132. The multiple auxiliary vehicles 162 move simultaneously and stop simultaneously.

In this embodiment, the first sub-lane 132 is adjacent to the testee, and the second sub-lane 133 is far away from the testee, thus the unexpectedness of the virtual stress event in which the testing vehicle 163 touches the testee is enhanced, thereby making the acquired stress reaction data more realistic.

In an embodiment of the present application, the step S600 further includes the following steps.

At step S640, control an interference vehicle 164 and/or a virtual pedestrian 165 to present in a visual field range 166 of the testee, to attract the testee's attentions when the testing vehicle 163 is travelling.

Specifically, as shown in FIG. 4, the interference vehicle 164 may appear in the visual field range 166 of the testee. When the interference vehicle 164 on the second lane 140 turns right and travels to the first lane 130, it enters into the visual field range 166 of the testee and attracts the testee's attention. The virtual pedestrian 165 appears in the test-waiting zone 110 and gradually moves toward the test zone 120, to enter into the visional field range 166 of the testee to attract the testee's attentions. The interference vehicle 164 and the virtual pedestrian 165 may appear simultaneously, or only the interfering vehicle 164 or only the virtual pedestrian 165 appears.

In this embodiment, the interference vehicle 164 and/or the virtual pedestrian 165 are controlled to appear in the visual field range 166 of the testee, such that the interference vehicle 164 and/or the virtual pedestrian 165 can effectively attract the testee's attentions when the testing vehicle 163 is travelling. Further, cooperating with the blocking of the auxiliary vehicle 162, the interference vehicle 164 and/or the virtual pedestrian 165 disable the testee to be aware of the testing vehicle 163, thereby enhancing the unexpectedness of the virtual stress event, and making the acquired stress reaction data more realistic.

In an embodiment of the present application, the stress reaction data include one or more of motion feature data, physiological electrical signals, and plantar pressure data.

Specifically, the motion feature data include one or more of a speed of the testee, a movement acceleration of the testee, and a displacement of the testee relative to the ground. The physiological electrical signals include one or more of electroencephalograms and muscle surface electromyographies. The plantar pressure data includes plantar pressure distribution data.

This embodiment, by acquiring multiple types of stress reaction data, can perform a full and comprehensive analysis for the stress reaction made by the human who is confronted by a danger signal.

In an embodiment of the present application, the step S500 further includes the following steps S520 to S540.

At step S520, if the visual field direction of the testee faces the test zone 120 in the virtual road traffic scene 100, then an instruction of starting acquiring the motion feature data is sent to a motion capture module 40, and an instruction of starting acquiring the physiological electrical signal is sent to a physiological electrical signal acquisition module 50, and an instruction of starting acquiring the plantar pressure data is sent to a plantar pressure test module 60.

Specifically, the time points at which the virtual scene control module 30 sends instructions of starting acquiring data to each module are not limited, only they are just before a time point at which the testee is stimulated.

At step S540, acquire, in real time, the motion feature data sent by the motion capture module 40, the physiological electrical signal sent by the electrical signal acquisition module 50, and the plantar pressure data sent by the plantar pressure test module 60.

Specifically, the virtual scene control module 30 can also periodically acquire the motion feature data, the physiological electrical signal, and the plantar pressure data after each preset acquisition time period.

In this embodiment, before the stimulation is applied to the testee, the instruction of starting acquiring the motion feature data is sent to the motion capture module 40; the instruction of starting acquiring the physiological electrical signal is sent to the physiological electrical signal acquisition module 50, and the instruction of starting acquiring the plantar pressure data is sent to the plantar pressure test module 60. Thus, the stress reaction data include both the reaction data of the testee stimulated and the reaction data of the testee in a normal state, thus forming a comparison beneficial to the analysis of the human stress reaction.

In an embodiment of the present application, the step S700 includes the following steps S710 to S720:

At step S710, start timing when the testing vehicle 163 touches the testee. After a preset time period, an instruction of interrupting acquisition of motion feature data is sent to the motion capture module 40; an instruction of interrupting acquisition of physiological electrical signals is sent to the physiological electrical signal acquisition module 50; and an instruction of interrupting acquisition of the plantar pressure data is sent to the plantar pressure test module 60.

Specifically, the preset time period is set by the tester.

At step S720, stop receiving the motion feature data sent by the motion capture module 40, the physiological electrical signal sent by the physiological electrical signal acquisition module 50, and the plantar pressure data sent by the plantar pressure test module 60.

Specifically, after stopping receiving the motion feature data, the physiological electrical signal, and the plantar pressure data, the testing steps end.

In this embodiment, after the stimulation to the testee lasts for the preset time period, the instruction of interrupting acquisition of the motion feature data is sent to the motion capture module 40, the instruction of interrupting acquisition of the physiological electrical signal is sent to the physiological electrical signal acquisition module 50, and the instruction of interrupting acquisition of the plantar pressure data is sent to the plantar pressure test module 60. Thus, the stress reaction data include both the reaction data of the testee stimulated and the reaction data of the testee in the normal state, thereby forming a comparison beneficial to the analysis of the human stress reaction.

The application also provides a testing system for a human stress reaction.

Figure 5:
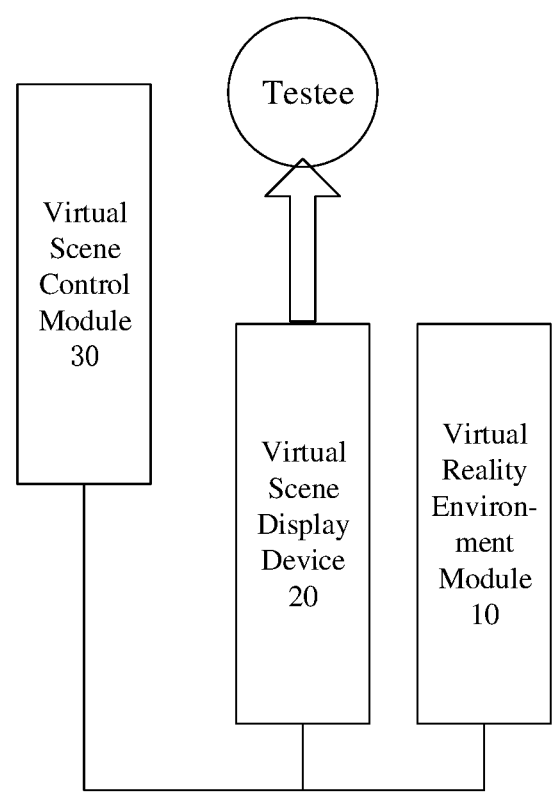
FIG. 5 is a schematic structural diagram illustrating a testing system for a human stress reaction according to an embodiment of the present application.
Figure 6:
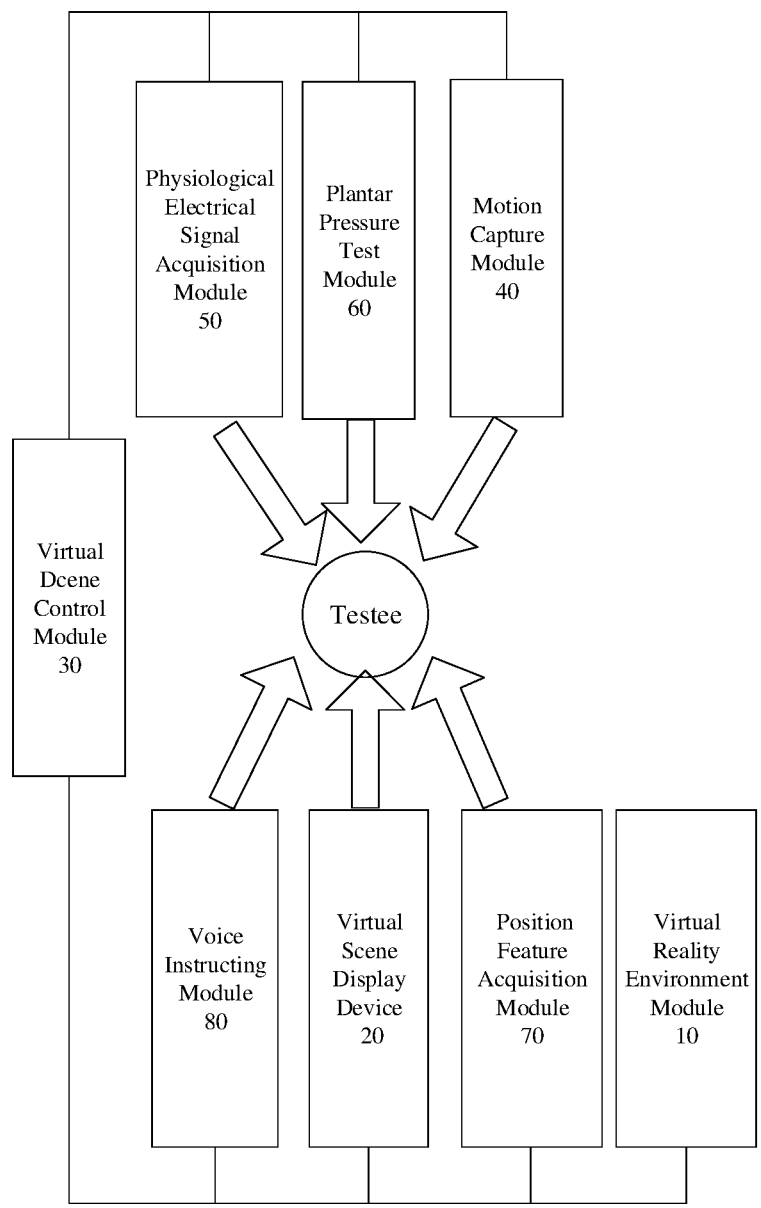
FIG. 6 is a schematic structural diagram illustrating a testing system for a human stress reaction according to another embodiment of the present application.

As shown in FIG. 5 and FIG. 6, in an embodiment of the present application, the testing system for the human stress reaction includes a virtual reality environment module 10, a virtual scene display device 20, a virtual scene control module 30, a motion capture module 40, and a physiological electrical signal acquisition module 50, a plantar pressure test module 60 and a voice instructing module 80.

The virtual scene control module 30 is connected to the virtual reality environment module 10 and the virtual scene display device 20 respectively. The motion capture module 40 is connected to the virtual scene control module 30. The physiological electrical signal acquisition module 50 is connected to the virtual scene control module 30. The plantar pressure test module 60 is connected to the virtual scene control module 30. The voice instructing module 80 is connected to the virtual scene control module 30.

The virtual reality environment module 10 is configured to establish a virtual road traffic scene 100. The virtual scene display device 20 is worn on the head of the testee. The virtual scene display device 20 is configured to present the virtual road traffic scene 100 in the brains of the testee. The virtual scene control module 30 is configured to execute the testing method for the human stress reaction mentioned above, thus controlling the reality environment module to create a virtual stress event, and applying a stimulation to the testee, to cause the testee to make a stress reaction.

The motion capture module 40 is arranged on the limbs and/or the torso of the testee. The motion capture module 40 is configured to acquire the motion feature data of the testee during the stress reaction made by the testee and send the motion feature data to the virtual scene control module 30. The physiological electrical signal acquisition module 50 is arranged on the skin surface of the testee. The physiological electrical signal acquisition module 50 is configured to acquire the physiological electrical signal of the testee during the stress reaction made by the testee and send the physiological electrical signal to the virtual scene control module 30. The plantar pressure test module 60 is attached to the plantar of the testee. The plantar pressure test module 60 is configured to acquire the plantar pressure data of the testee during the stress reaction made by the testee and send the plantar pressure data to the virtual scene control module 30. The voice instructing module 80 is configured to send out a voice instruction under the control of the virtual scene control module 30, to instruct the testee to perform an action.

Specifically, the virtual scene control module 30 can include a human-machine interaction interface. A tester can control the virtual scene control module 30 through the human-machine interaction interface, so as to send control instructions to other modules in the testing system for the human stress reaction.

The motion capture module 40 includes a plurality of markers (marker points). A surface of each maker is provided with a special reflective material. The plurality of markers are attached to the surfaces of the limbs and/or the torso of the testee. The plurality of markers can acquire motion feature data of the testee at an information acquisition frequency higher than 100 Hz the moment the stress reaction occurs.

The physiological electrical signal acquisition module 50 includes an electroencephalogram signal acquisition unit and a surface electromyography signal acquisition unit. The electroencephalogram signal acquisition unit includes an electrode plate and electrode paste. The electrode plate is attached to the head of the testee. The electrode plate is connected to the cerebral cortex through the electrode paste, to acquire the electroencephalogram signal created by the testee in the process of stress perception and in the process of stress decision. The surface electromyography signal acquisition unit includes electrode plates attached to the surface of the main muscle groups of the testee. When the testee is stimulated by stress, the muscles of the testee exert forces, and the surface electromyography signal acquisition unit can acquire electrical signals of the muscle epidermis at a frequency higher than 2000 Hz. The surface electromyography signal acquisition unit is configured to judge the activation level of the main muscle groups of the testee under a stress reaction.

The plantar pressure test module 60 can include a plurality of thin-film pressure sensors. The plurality of thin-film pressure sensors can be mounted on the insole of the testee. When the testee make a stress reaction, the plurality of thin-film pressure sensors can acquire, in real time, the distribution of the foot pressure exerted on the ground during the movement of the testee.

The testee wears a position feature acquisition module 70, which is configured to acquire position information and visual field information of the testee in the virtual road traffic scene 100, when the testee makes a stress reaction. Specifically, the position feature acquisition module 70 can include a locator. The locator is connected to the virtual scene control module 30. When the testee makes a stress reaction, the locator can acquire, in real time, the position information of the testee in the virtual road traffic scene 100, and sends it to the virtual scene control module 30.

The position feature acquisition module 70 can include a visual field detection device. The visual field detection device can be worn on the head of the testee, and is configured to acquire the visual field information of the testee in the virtual road traffic scene 100 in real time. The visual field information can include a visual field direction and/or a visual field range of the testee. The visual field detection device can acquire the visual field information in multiple ways. Optionally, the visual field detection device can acquire a motion track of the pupils of the testee, so as to determine the visual field information.

In addition, the testing system for the human stress reaction can further include a reality detection site. The reality detection site can include a reality activity area. The reality activity area can include a test-waiting activity area and a test activity area. The test-waiting activity area corresponds to the test-waiting zone 110. The test activity area corresponds to the test zone 120. The test activity area can be a test field of 15 m×5 m. A plurality of optical motion capture cameras can be provided at the edge of the test activity area. The plurality of optical motion capture cameras are used in conjunction with the motion capture module 40, to acquire motion feature data of the testee.

In this embodiment, the virtual road environment scene 100 is established by providing the virtual reality environment module 10, such that the testee can subconsciously make a real stress reaction in an emergency. By arranging the virtual scene display device 20, the virtual road traffic scene 100 is presented in the brain of the testee. By arranging the virtual scene control module 30, the virtual road traffic scene 100 is changed, and a virtual stress event is created to stimulate the testee, such that the testee makes a stress reaction. By arranging the motion capture module 40, the motion feature data of the testee are acquired in the process of the testee stress reaction. By arranging the physiological electrical signal acquisition module 50, the physiological electrical signals of the testee are acquired in the process of the testee stress reaction. By arranging the plantar pressure test module 60, the plantar pressure data of the testee are acquired in the process of the testee stress reaction. The testing system for the human stress reaction provided by the present application, which is based on virtual reality technology, can create a real stimulation to the testee, such that the testee makes a real stress reaction.

All technical features in the embodiments can be arbitrarily combined. For purpose of simplifying the description, not all arbitrary combinations of the technical features in the embodiments illustrated above are described. However, as long as such combinations of the technical features are not contradictory, they should be considered to be within the scope of the specification of the disclosure.

The above embodiments are merely illustrations of several implementations of the present application, and the description thereof is more specific and detailed, but should not be deemed as limitations to the scope of the present application. It should be noted that, for those skilled in the art, various deformations and improvements can be made without departing from the concepts of the present application. All these deformations and improvements are within the protection scope of the present application. Therefore, the protection scope of the present application is defined by the appended claims.

What is claimed is:

1. A testing method for a human stress reaction, comprising:
   sending a request for establishing a virtual road traffic scene to a virtual reality environment module;
   acquiring position information and visual field information of a testee in the virtual road traffic scene after the virtual reality environment module establishes the virtual road traffic scene;
   guiding the testee into a test zone when the testee is within a test-waiting zone in the virtual road traffic scene and when a visual field direction of the testee faces the test zone in the virtual road traffic scene, and starting acquiring stress reaction data of the testee simultaneously; and
   controlling the virtual reality environment module to create a virtual stress event in the test zone after it is determined that the testee is within the test zone, and applying a stimulation to the testee, to cause the testee to make a stress reaction.

2. The testing method for the human stress reaction of claim 1, further comprising:
   determining whether the testee is within the test-waiting zone in the virtual road traffic scene based on the position information.

3. The testing method for the human stress reaction of claim 2, further comprising:
   determining whether the visual field direction of the testee faces the test zone in the virtual road traffic scene based on the visual field information when the testee is within the test-waiting zone in the virtual road traffic scene.

4. The testing method for the human stress reaction of claim 3, further comprising:
   interrupting acquisition of the stress reaction data after the testee is continuously stimulated for a preset time period.

5. The testing method for the human stress reaction of claim 4, wherein the virtual road traffic scene comprises a first lane;
   the first lane extends in a first direction; the first lane comprises a plurality of sub-lanes arranged in parallel with each other; and each of the sub-lanes extends in the first direction.

6. The testing method for the human stress reaction of claim 5, wherein the virtual road traffic scene further comprises a second lane;
   the second lane extends in a second direction; the first direction is perpendicular to the second direction; and the first lane and the second lane intersect to form an intersection.

7. The testing method for the human stress reaction of claim 6, wherein the test zone is disposed on the first lane; the test zone extends in the second direction and runs across the first lane; the test zone is configured to guide the testee across the first lane safely; the test zone is arranged to be adjacent to the intersection.

8. The testing method for the human stress reaction of claim 7, wherein the virtual road traffic scene further comprises traffic lights;

the traffic lights are disposed in the test zone and configured to show the testee a traffic situation of the test zone.

9. The testing method for the human stress reaction of claim 8, wherein steps of guiding the testee into the test zone when the visual field direction of the testee faces the test zone in the virtual road traffic scene, and starting acquiring the stress reaction data of the testee simultaneously, comprise:

sending an instruction to the virtual reality environment module when the visual field direction of the testee faces the test zone in the virtual road traffic scene; controlling the traffic lights to show an impassable state; controlling an auxiliary vehicle to appear and to travel on a first sub-lane of the first lane at a first preset travelling speed;

acquiring a position of the auxiliary vehicle; calculating a straight-line distance from the position of the auxiliary vehicle to the test zone in the first direction based on the position of the auxiliary vehicle;

determining whether the straight-line distance from the position of the auxiliary vehicle to the test zone is greater than a preset distance;

controlling the auxiliary vehicle to stop travelling, and controlling the traffic lights to show a passable state, when the straight-line distance from the position of the auxiliary vehicle to the test zone is less than or equal to the preset distance; and sending an instruction to a voice instructing module; controlling the voice instructing module to send out a voice instruction, to guide the testee across the test zone.

10. The testing method for the human stress reaction of claim 9, wherein the steps of guiding the testee into the test zone, when the visual field direction of the testee faces the test zone in the virtual road traffic scene, and starting acquiring the stress reaction data of the testee simultaneously, further comprise:

controlling the auxiliary vehicle to continue to travel when the straight-line distance from the position of the auxiliary vehicle to the test zone is greater than the preset distance, till the straight-line distance from the position of the auxiliary vehicle to the test zone is less than or equal to the preset distance.

11. The testing method for the human stress reaction of claim 10, wherein steps of controlling the virtual reality environment module to create the virtual stress event in the test zone after it is determined that the testee is within the test zone, and applying the stimulation to the testee, to get the testee make the stress reaction, further comprise:

setting a target location point in the test zone, wherein the target location point is one of a plurality of intersection points formed by the sub-lanes intersecting with the test zone;

acquiring the position information of the testee and a walking speed of the testee, and calculating a time taken for the testee to reach the target location point; and controlling a testing vehicle to appear at an initial position of the testing vehicle and travel on a second sub-lane at a uniform speed of a second preset speed based on the time taken the testee to reach the target location point, to enable the testing vehicle to touch the testee at the target location point.

12. The testing method for the human stress reaction of claim 11, wherein the initial position of the testing vehicle is disposed on the second sub-lane, and the second sub-lane intersects with the test zone to form the target location point.

13. The testing method for the human stress reaction of claim 12, wherein the straight-line distance from the initial position of the testing vehicle to the target location point satisfies following equations, enabling the testing vehicle to touch the testee at the target location point:

$$\begin{cases} X = X_1 + X_2 = V_0 t_1 + \dfrac{V_0^2 - V_1^2}{2a} \\ t = t_1 + t_2 = t_1 + \dfrac{V_0 - V_1}{a} \end{cases}$$

wherein, X is the straight-line distance from the initial position of the testing vehicle to the target location point; $X_1$ is a first travelling distance of the testing vehicle before it brakes; $X_2$ is a second travelling distance of the testing vehicle after it brakes; $V_0$ is a second preset speed; $V_1$ is a speed of the testing vehicle when it reaches the target location point; $t_1$ is a travelling time of the testing vehicle before it brakes; $t_2$ is a braking time of the testing vehicle; a is a braking deceleration of the testing vehicle; and t is the time taken for the testee to reach the target location point.

14. The testing method for the human stress reaction of claim 13, wherein the first sub-lane is adjacent to the testee; the second sub-lane is far away from the testee, making the auxiliary vehicle hide the testing vehicle when the testing vehicle is traveling.

15. The testing method for the human stress reaction of claim 14, wherein the step of controlling the virtual reality environment module to create the virtual stress event in the test zone after it is determined that the testee is within the test zone, and applying the stimulation to the testee, such that the testee make the stress reaction, further comprises:

controlling an interference vehicle and/or an virtual pedestrian to present in a visual field range of the testee, to attract the testee's attentions when the testing vehicle is travelling.

16. A testing system for a human stress reaction, comprising:

a virtual reality environment module configured to establish a virtual road traffic scene;

a virtual scene display device worn on a head of a testee and configured to present the virtual road traffic scene in a brain of the testee; and a virtual scene control module connected to the virtual reality environment module and the virtual scene display device respectively and comprising a storage and one or more processors, wherein computer-readable instructions are stored in the storage, and when the computer-readable instructions are executed by the one or more processors, the one or more processors perform steps of:

sending a request for establishing the virtual road traffic scene to the virtual reality environment module;

acquiring position information and visual field information of the testee in the virtual road traffic scene after the virtual reality environment module establishes the virtual road traffic scene;

guiding the testee into a test zone when the testee is within a test-waiting zone in the virtual road traffic scene and when a visual field direction of the testee faces the test zone in the virtual road traffic scene, and starting acquiring stress reaction data of the testee simultaneously;

controlling the virtual reality environment module to create a virtual stress event in the test zone after it is determined that the testee is within the test zone, and applying a stimulation to the testee, such that the testee make a stress reaction.

\* \* \* \* \*